United States Patent
Armstrong et al.

(10) Patent No.: US 12,286,396 B2
(45) Date of Patent: Apr. 29, 2025

(54) DICARBOXYLIC ACID COMPOUNDS, INORGANIC PARTICLES TREATED WITH THE DICARBOXYLIC ACID COMPOUNDS, AND COMPOSITIONS THEREOF

(71) Applicant: 3M INNOVATIVE PROPERTIES COMPANY, St. Paul, MN (US)

(72) Inventors: Paul B. Armstrong, St. Paul, MN (US); Jonathan A. Anim-Addo, New Hope, MN (US); Bryan V. Hunt, Nowthen, MN (US); Evan L. Schwartz, Vadnais Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 570 days.

(21) Appl. No.: 17/753,993

(22) PCT Filed: Sep. 25, 2020

(86) PCT No.: PCT/IB2020/058985
§ 371 (c)(1),
(2) Date: Mar. 21, 2022

(87) PCT Pub. No.: WO2021/064530
PCT Pub. Date: Apr. 8, 2021

(65) Prior Publication Data
US 2023/0339852 A1 Oct. 26, 2023

Related U.S. Application Data

(60) Provisional application No. 62/908,309, filed on Sep. 30, 2019.

(51) Int. Cl.
| | | |
|---|---|---|
| C07C 323/52 | (2006.01) |
| B82Y 30/00 | (2011.01) |
| C07D 307/91 | (2006.01) |
| C09C 1/00 | (2006.01) |
| C09C 1/04 | (2006.01) |
| C09C 1/36 | (2006.01) |
| C09C 3/08 | (2006.01) |

(52) U.S. Cl.
CPC .......... *C07C 323/52* (2013.01); *C07D 307/91* (2013.01); *C09C 1/04* (2013.01); *C09C 3/08* (2013.01); *B82Y 30/00* (2013.01); *C01P 2004/64* (2013.01); *C09C 1/00* (2013.01); *C09C 1/3669* (2013.01)

(58) Field of Classification Search
CPC .......... C07C 323/52; C09C 3/08; C09C 1/00; C09C 1/3669
See application file for complete search history.

(56) References Cited

U.S. PATENT DOCUMENTS

| | | |
|---|---|---|
| 4,576,850 A | 3/1986 | Martens |
| 8,821,770 B2 | 9/2014 | Jones |
| 9,382,128 B2 | 7/2016 | Edwards |
| 10,234,763 B2 | 3/2019 | Owusu-Nkwantabisah |

FOREIGN PATENT DOCUMENTS

| | | |
|---|---|---|
| CN | 110387000 | 10/2019 |
| WO | WO 2003-095568 | 11/2003 |
| WO | WO 2008-121465 | 10/2008 |
| WO | WO 2015-153148 | 10/2015 |
| WO | WO 2016-168147 | 10/2016 |
| WO | WO 2017-030857 | 2/2017 |
| WO | WO 2017-142782 | 8/2017 |
| WO | WO 2017-172462 | 10/2017 |
| WO | WO 2018-122748 | 7/2018 |
| WO | WO 2019-023096 | 1/2019 |

OTHER PUBLICATIONS

International Search Report for PCT Application No. PCT/IB2020/058985, mailed on Dec. 9, 2020, 5 pages.

*Primary Examiner* — Kregg T Brooks
*Assistant Examiner* — David R. Foss
(74) *Attorney, Agent, or Firm* — Jeffrey M. Olofson

(57) ABSTRACT

Described herein is a dicarboxylic acid compound of formula (I): Wherein: $R^3$ comprises an aryl group, $R^2$ is an alkylene group comprising 1 to 6 carbon atoms, n is 0 or 1, $R^1$ is H or $CH_3$, and X is S or NZ, wherein Z is H, an alkyl group comprising 1 to 4 carbon atoms or a phenyl group. Such compounds can be used to modify the surface of inorganic particles. These modified inorganic particles may then be advantageously used in polymerizable resins to increase the refractive index of the resulting composite, while enabling good flow properties of the polymerizable composition.

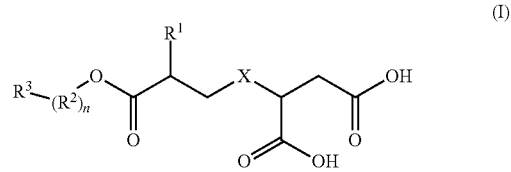

(I)

19 Claims, No Drawings

DICARBOXYLIC ACID COMPOUNDS, INORGANIC PARTICLES TREATED WITH THE DICARBOXYLIC ACID COMPOUNDS, AND COMPOSITIONS THEREOF

CROSS REFERENCE TO RELATED APPLICATIONS

This application is a national stage filing under 35 U.S.C. 371 of PCT/IB2020/058985, filed Sep. 25, 2020, which claims the benefit of U.S. Provisional Patent Application No. 62/908,309, filed Sep. 30, 2019, the disclosure of which is incorporated by reference in its/their entirety herein.

TECHNICAL FIELD

Dicarboxylic acid compounds functionalized with aromatic groups are disclosed. Also disclosed is the method of treating an inorganic particle with the dicarboxylic acid compounds to form a surface-treated inorganic particle. Such surface modified inorganic particles have a high refractive index and can be used in polymeric resins for optical applications.

SUMMARY

There is a desire to identify surface treatments for inorganic particles, which can provide improved handling and/or performance in polymeric compositions.

In one aspect, a dicarboxylic acid compound is described. The dicarboxylic acid compound is of formula (I):

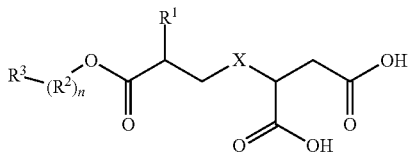

wherein:
$R^3$ comprises an aryl group,
$R^2$ is an alkylene group comprising 1 to 6 carbon atoms,
n is 0 or 1,
$R^1$ is H or $CH_3$, and
X is S or NZ, wherein Z is H, an alkyl group comprising 1 to 4 carbon atoms, or a phenyl group.

In another aspect, a method of surface treating an inorganic particle is described, the method comprising: contacting the surface of the inorganic particle with the dicarboxylic acid compound as described above.

In yet another aspect, a surface modified inorganic particle is described, wherein the surface of an inorganic particle is modified with a plurality of the following groups of Formula II:

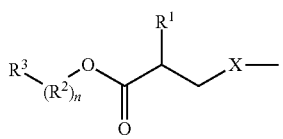

Wherein
$R^3$ comprises an aryl group,
$R^2$ is an alkylene group comprising 1 to 6 carbons,
n is 0 or 1,
$R^1$ is H or $CH_3$, and
X is S or NZ, wherein Z is H, an alkyl group comprising 1 to 4 carbon atoms, or a phenyl group.

In yet another aspect, a polymerizable composition is described comprising the surface modified inorganic particle from above with an aromatic monomer.

The above summary is not intended to describe each embodiment. The details of one or more embodiments of the invention are also set forth in the description below. Other features, objects, and advantages will be apparent from the description and from the claims.

DETAILED DESCRIPTION

For the following defined terms, these definitions shall be applied, unless a different definition is given in the claims or elsewhere in this specification.

The terms "a", "an", and "the" are used interchangeably and mean one or more.

The term "and/or" is used to indicate one or both stated cases may occur, for example A and/or B includes, (A and B) and (A or B).

The term "(meth)acrylate" refers to monomeric acrylic or methacrylic esters of alcohols. Acrylate and methacrylate monomers or oligomers are referred to collectively herein as "(meth)acrylates".

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "phenyl" refers to a cyclic aromatic group of formula $-C_6H_5$.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms.

The term "agglomeration" is used according to its commonly understood definition as defined by IUPAC, where agglomeration is synonymous with flocculation and according to the IUPAC definition, flocculation is "a process of contact and adhesion whereby the particles of a dispersion form larger-size clusters".

The terms "room temperature" and "ambient temperature" are used interchangeably and have their conventional meaning, that is to say a temperature of from 20-25° C. The term "ambient conditions" has its conventional meaning, with regard to temperatures (e.g., 20-25° C.) and pressures (e.g., 98-104 kiloPascals).

The recitation of numerical ranges by endpoints includes all numbers subsumed within that range (e.g., 1 to 10 includes 1.4, 1.9, 2.33, 5.75, 9.98, etc.).

The recitation of "at least one" includes all numbers of one and greater (e.g., at least 2, at least 4, at least 6, at least 8, at least 10, at least 25, at least 50, at least 100, etc.).

As used herein, the phrase "comprising at least one of" followed by a list refers to comprising any one of the items in the list and any combination of two or more items in the list. The phrase "at least one of" followed by a list refers to any one of the items in the list or any combination of two or more items in the list. As used herein, "comprises at least one of" A, B, and C refers to element A by itself, element B by itself, element C by itself, A and B, A and C, B and C, and a combination of all three.

Optical devices are becoming increasingly complex, which impacts the materials used in them. For example, as optical devices have become more compact, they often include multiple layers, resulting in a growing need for thinner layers. Among the properties that are becoming increasingly important is refractive index. As light travels through the layers of a multilayer article, it encounters the interface between layers. If the refractive indices of the layers are different, light can be refracted or reflected. Therefore, to minimize this effect, matching of the refractive indices of layers within a multilayer article is desirable.

The present disclosure is directed toward dicarboxylic acid compounds comprising aryls that can be used to modify the surface of inorganic particles. These surface modified inorganic particles have advantages over other surface modified inorganic particles, in that they can have improved stability and/or more of the surface modified inorganic particles can be added to polymerizable compositions, while still allowing the polymerizable composition to have sufficiently low viscosity for subsequent processing.

Dicarboxylic Acid Compounds

The dicarboxylic acid compounds of the present disclosure are of Formula (I):

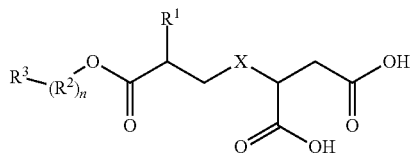

(I)

Wherein X is S or NZ, wherein Z is H, a phenyl group, or alkyl group comprising 1, 2, 3, or 4 carbon atoms. The alkyl group may be linear or branched. Exemplary alkyl groups include —$CH_3$, —$CH_2CH_3$, —$CH(CH_3)_2$, —$CH_2CH_2CH_3$, —$CH_2CH(CH_3)CH_3$, and —$CH_2CH_2CH_2CH_3$.

$R^1$ is H or $CH_3$.

The subscript "n" is 0 or 1 and $R^2$ is a divalent alkylene group comprising 1, 2, 3, 4, 5, or 6 carbon atoms. The alkylene group may be linear or branched. Exemplary alkylene groups include: —$(CH_2)_m$— wherein m is 1, 2, 3, 4, 5, or 6; —$CH(CH_3)CH_2$—; —$CH_2CH(CH_3)CH_2$—; —$CH_2CH(CH_2CH_3)CH_2$—; and —$CH_2CH(CH_3)CH_2CH(CH_3)$—.

$R^3$ is a monovalent group which comprises at least one aryl group, for example one aryl group, two aryl groups, or even three aryl groups. Each aryl group may comprise one or more aromatic rings.

In one embodiment, $R^3$ is an aryl group. In another embodiment, $R^3$ comprises moieties in addition to the at least one aryl group. Such moieties include an arylene group having 5, 6, or 8 carbon atoms; an alkylene group having 1, 2, 3, 4, 5, or 6 carbon atoms, and/or a heteroatom such as oxygen (e.g., ether linkage), nitrogen (e.g., amine linkage), or sulfur (e.g., thioether linkage). In one embodiment, $R^3$ does not contain Si atoms.

In one embodiment, $R^3$ comprises at least one 6-membered aromatic ring such as a phenyl, phenoxy, biphenyl, naphthyl, thiophenyl, carbazole, cumyl phenoxyl (bisphenol A), benzyl phenyl, phenyl benzyl, phenoxy phenyl, fluorenyl, thiophenyl benzyl, dibenzofuran, or combinations thereof.

In one embodiment, n is 1 or 2 and $R^3$ is a phenyl, phenoxy phenyl, cumyl phenoxy, benzyl phenyl, naphthyloxy, benzophenone oxy, fluorenyl, thiophenylphenyl, diphenyl phenoxy, carbazole, or thionaphthyl group.

In another embodiment, n is 0 and $R^3$ is a phenyl, benzyl phenyl, biphenyl, fluorenyl, or naphthyl group.

Exemplary compounds according to Formula I include:

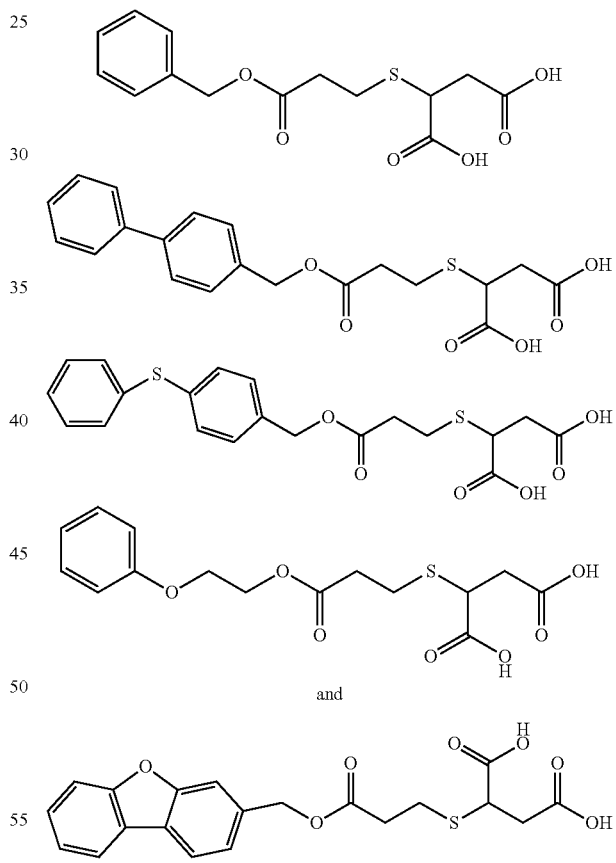

and

The compounds of Formula I may be synthesized, for example, as follows. A mercaptosuccinic acid can, in a Michael addition reaction, be reacted with an aromatic (meth)acrylate in the presence of a base catalyst to form the compounds of Formula I. This enables the modification of the surface of the particles with (meth)acrylates that are desirable for use in high refractive index polymerizable compositions. Alternatively, an aromatic alcohol could be esterified with mercaptopropionic acid, followed by a Michael reaction with maleic anhydride and hydrolysis to form an equivalent aromatic diacid.

Inorganic Particles

The dicarboxylic acid compounds disclosed above may be used to modify the surface of inorganic particles.

The particles of the present disclosure prior to modification are inorganic and comprise a metal oxide, a chalcogenide, or combinations thereof. The inorganic particles are free or substantially free of C—H bonds (meaning that there are less than 10, 5, 1, 0.5, or even 0.1% by mass of C—H groups by mass of the inorganic particles).

In one embodiment, the inorganic particles prior to modification have a refractive index of at least 1.70, 1.75, 1.80, 1.85, 1.90, 1.95, 2.00, 2.10, 2.20, 2.30, 2.40, 2.50, 2.60, 2.70, or even 2.80, and no more than 3.50, or even 4.00.

Exemplary metal oxide particles include the following titanium, aluminum, hafnium, zinc, tin, cerium, niobium, yttrium, indium, antimony, and zirconium oxides, as well as mixed metal oxides such as, for example, indium tin oxide. Among the more desirable metal oxide particles are those metals of titanium, zinc, and/or zirconium. In many instances a single type of metal oxide particle is used, but mixtures of metal oxide particle may also be used.

Exemplary chalcogenides include zinc sulfide, zinc selenide, and iron sulfide.

The size of the inorganic particles can vary depending on the application. In one embodiment, the particles have an average primary (i.e., individual) particle diameter and/or secondary (i.e., agglomeration) particle diameter of at least 2, 5, 10, 20, or even 25 nm and at most 40, 50, 80, 100, 150, 200, 250, 300, 500, 750, or even 1000 nm (nanometer). The particle diameter measurements can be based on transmission electron microscopy (TEM) or dynamic light scattering (DLS). It is preferable that the particles are not agglomerated and remain so over time.

In optical applications, the diameter of the inorganic particles should be sufficiently small to not be visible to the unaided human eye. In one embodiment, the inorganic particles can be particles having an average primary particle diameter and/or secondary particle diameter of greater than 1, 5, or even 10 nm. The primary and/or secondary particle diameter is generally less than 100, 75, or even 50 nm. Typically, the primary and/or secondary particle diameter is less than 40 nm, 30 nm, or 20 nm. To ensure transparency, the inorganic particles should have an average diameter of at most 50 nm.

Exemplary nanoparticles of zirconium dioxide are available from Nalco Chemical Co. under the trade designation "NALCO OOSSO08" and from Buhler AG Uzwil, Switzerland under the trade designation "BUHLER ZIRCONIA Z-WO SOL". Nanoparticles of titanium dioxide containing a mixture of anatase and brookite crystal structures are commercially available from Showa Denko Corp. of Japan as "NTB-1". Nyacol Nano Technologies, Ashland MA, supplies nanoparticles of zirconium dioxide as well as titanium dioxide, as does Sukgyung AT, Des Plaines, IL.

The inorganic particles are solid, meaning they do not comprise a hollow center. However, the inorganic particles may contain imperfections, such as low amounts (e.g., less than 20, 10, or even 5%) of undesired bubbles, but imperfections are not preferable.

In one embodiment, the inorganic particles used in the present disclosure may be substantially spherical. The degree of sphericity of a particle is the ratio of the surface area of a sphere of set volume to the surface area of that particle with the same volume. Substantially spherical means that the average degree of sphericity is at least 0.75, 0.8, 0.85, 0.9, 0.95, or even 0.99, with the theoretical sphericity of 1.0 for a perfect sphere.

In one embodiment, the inorganic particles have a narrow polydispersity index, for example, less than 2, 1.5, or even 1.0 when measured using standard particle size measurement techniques such as microscopy or light scattering.

The metal oxides and chalcogenides can exist in distinct crystalline forms. For example, titanium oxide can exist in rutile, anatase, and brookite crystal structures; zirconium dioxide can exist in monoclinic, tetragonal, and cubic crystal structures; zinc sulfide can exist in wurzite and sphalerite crystal structures; and iron sulfide can exist in pyrite, and Marcasite crystal structures. These different crystalline forms may have different refractive indices, for example rutile has a refractive index of 2.609, anatase 2.488, and brookite 2.583. In one embodiment, the inorganic particles may comprise mixtures of crystal structure of the same inorganic compound.

Fully condensed inorganic particles disclosed herein typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g., zirconia) particles have a high refractive index whereas amorphous particles typically have a lower refractive index.

Surface Modified Inorganic Particles

The surface of the inorganic particles described herein can be modified with the dicarboxylic acid compounds according to Formula (I) to form surface treated inorganic particles. The modified inorganic particles of the present disclosure are substantially free of Si atoms, meaning the modified inorganic particles are not made with silica particles nor are silane surface treatments used to modify the inorganic particles with the organic groups. The inorganic particle may comprise small amounts of metal, or metalloid impurities, such as Si atoms. In one embodiment, the modified inorganic particles comprise less than 5000, 1000, 500, 100, 50, 20 or even 10 parts per million of Si atoms.

Although not wanting to be limited by theory, it is believed that the dicarboxylic acid compound interacts with the surface of the inorganic particle to form a surface treated inorganic particle having a plurality of groups represented by Formula II:

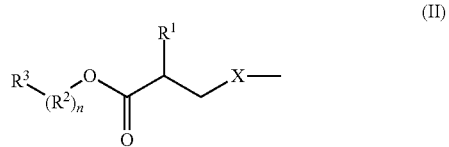

(II)

wherein
$R^3$ comprises an aryl group as described above for the dicarboxylic acid compound (Formula (I)),
$R^2$ is a divalent alkylene group comprising 1 to 6 carbons as described above for the dicarboxylic acid compound,
n is 0 or 1,
$R^1$ is H or $CH_3$, and
X is S or NZ, wherein Z is H, an alkyl group comprising 1 to 4 carbon atoms, or a phenyl group as described above for the dicarboxylic acid compound.

Exemplary groups according to Formula II include:

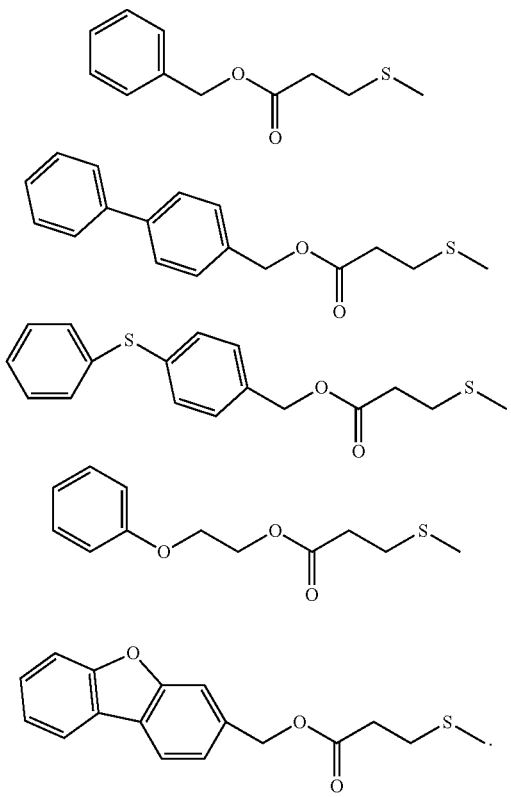

In one embodiment, the modified inorganic particles comprises at least 5, 10, 15, 20, 25, 30, 35, or even 40% by weight of the groups represented by Formula II. In one embodiment, the surface modified inorganic particles comprises no more than 30, 40, 50, 60, 70, 75, 80, or even 85% by weight of the groups represented by Formula II.

In one embodiment, at least 40, 45, 50, or even 60% and at most 70, 75, 80, 90, 95, or even 100% of the surface of the inorganic particles is modified with Formula II.

The surface modification of the inorganic particles can be accomplished in a variety of ways. The process generally involves combining a dispersion of the unmodified inorganic particle in water with the dicarboxylic acid of Formula (I). A solvent can enhance the solubility of the dicarboxylic acids of Formula (I) as well as the surface modified particles. Exemplary solvents include. 1-methoxy-2-propanol, ethanol, isopropanol, ethylene glycol, N,N-dimethylacetamide and 1-methyl-2-pyrrolidinone. The dispersion comprising the inorganic particles and the dicarboxylic acid of Formula (I) can be reacted at room temperature or an elevated temperature, with or without mixing. After surface modification, water can be removed by distillation to yield a dispersion of modified inorganic particles in solvent.

Alternatively, the inorganic particles can be surface modified via extraction. This process generally involves dissolving the dicarboxylic acid of Formula (I) in a solvent that is immiscible with water. Exemplary solvents include toluene, heptane, hexanes, diethyl ether, and ethyl acetate. An aqueous dispersion of inorganic particles is contacted with the solution of dicarboxylic acid, causing the particles to transfer from the water phase to the solvent phase. The extraction can be accelerated by mixing and/or running at elevated temperature. After surface modification, the water phase can be removed using a separatory funnel to yield a dispersion of modified inorganic particles in solvent.

In one embodiment, when surface modifying the inorganic particles at least 10, 20, 30 or even 40% by weight of the compound according to Formula I is used versus the weight of the inorganic particle. In one embodiment, when surface modifying the inorganic particles at most 50, 60, 70, or even 80% by weight of the compound according to Formula I is used versus the weight of the inorganic particle.

Polymerizable Compositions

The surface treated inorganic particles disclosed above can be used in a polymer composition to form a composite. For example, the surface treated inorganic particles can be combined with polymerizable (or curable) components to form a polymerizable composition, which can be subsequently polymerized (or cured) to form an article.

As used herein "polymerizable composition" refers to the total composition including an organic component and the surface modified inorganic particles described above. The "organic component" refers to all the components of the composition except for the surface modified inorganic particles. Since the surface treatments are generally adsorbed or otherwise attached (e.g., covalently bound) to the surface of the inorganic particles, the surface treatments are not considered a portion of the organic component.

Surface modified inorganic particles are used to increase the refractive index of the resulting polymeric article. In one embodiment, the refractive index of the surface modified inorganic particle is at least 2.0, 2.2, or even 2.4; and at most 2.6 or even 2.8. However, the addition of surface modified inorganic particles can increase the viscosity of the polymerizable composition, limiting the mass percent of particles that can be used. Therefore, the amount of surface modified inorganic particles present in the polymerizable composition can vary, based on the viscosity requirements of the application (e.g., coating or casting a film). In one embodiment, the surface modified inorganic particles are present in the polymerizable resin or resulting cured article in an amount of at least 2.0, 3.0, 4.0, or even 5.0 wt %; and at most 8.0, 10, 20, 25, 30, 35, or even 40 wt % based on the total weight. In another embodiment, the surface modified inorganic particles are present in the polymerizable resin or resulting cured article in an amount of at least 10 wt %, 20 wt %, 30 wt % or 40 wt %; and at most 50, 60, or even 70 wt % based on the total weight.

Generally, the organic component, before polymerization and/or after polymerization, has a refractive index of at least 1.3, 1.4, or even 1.45; and at most 1.7. The addition of the surface modified inorganic particles increases the refractive index of the polymerizable composition. In one embodiment, the addition of the surface modified particles to the organic composition increases the refractive index of the polymerizable composition and/or the polymerized composition by at least 0.1, 0.2, or even 0.3. Generally, the more surface modified particles added, the higher the refractive index of the polymerizable composition and the polymerized composition. In one embodiment, the refractive index of the polymerizable composition and/or the polymerized composition is at least 1.650, 1.670, 1.680, 1.690, 1.700, 1.720, 1.750, 1.800, 1.850, 1.900, or even 1.950.

As mentioned above, the addition of inorganic particles to the organic component in the absence of solvent can impact the viscosity of the polymerizable composition. In the present disclosure it has been discovered that the surface treatments disclosed herein enable high particle loading in the polymerizable composition, while still allowing a flowable composition, defined as a composition which has a viscosity of less than 10,000 cP (centipoise) when measured at ambient conditions using the method described below. The viscosity limitations may vary depending on the application, with some applications requiring a more viscous liquid. In one embodiment, the polymerizable composition has a viscosity, in the absence of solvent, at room temperature (e.g., 23° C.) of at least 5 or even 10 cP; and at most 20000, 10000, 5000, 2000, 1000, 500, 300, 100, 50, 30, or even 20 cP. In one embodiment, the polymerizable composition, in the absence of solvent, has a viscosity at 55° C. of at least 5 or 10 cP; and at most 5000, 2500, 2000, 1500, 1000, 500, 300, 100, 50, 30, or even 20 cP. In one embodiment, the polymerizable compositions of the present disclosure, achieve a lower viscosity, while maintaining the same or higher refractive index than surface modified inorganic particles not of the present disclosure. For example, in the absence of solvent, the polymerizable composition has a refractive index of at least 1.670 and a viscosity of no more than 400 cP at 55° C.; or for example, in the absence of solvent, the polymerizable composition has a refractive index of at least 1.680 and a viscosity of no more than 900 cP at 55° C. As used herein, viscosity is measured (at a shear rate up to 1000 sec$^{-1}$) with 25 mm parallel plates using a Dynamic Stress Rheometer. An absence of solvent, means that no solvent is deliberately added to the polymerizable composition.

In one embodiment, the polymerizable composition can be polymerized by conventional free radical polymerization methods.

The organic component typically comprises a mixture of ethylenically unsaturated monomers or oligomers. Preferably, the mixture comprises a major amount of a (e.g. aromatic) monofunctional (meth)acrylate monomer. A single monofunctional (meth)acrylate monomer may be used or a mixture of monofunctional (meth)acrylate monomers may be used. In one embodiment the monofunctional (meth)acrylate monomer has a low molecular weight (e.g. less than 450 g/mole). In one embodiment, the monofunctional (meth)acrylate monomer has a refractive index of at least 1.50, 1.51, 1.52, 1.53, 1.54, 1.55, 1.56, 1.57, 1.58, 1.59, 1.60, 1.61, or 1.62. In one embodiment, the monofunctional (meth)acrylate monomer has a refractive index of at most 1.65, 1.67, or even 1.68.

Exemplary aromatic monofunctional (meth)acrylate monomers include biphenyl monomers and substituted benzyl monomers.

Monofunctional biphenyl monomers comprise a terminal biphenyl group (wherein the two phenyl groups are not fused, but joined by a bond) or a terminal group comprising two aromatic groups joined by a linking group (e.g. Q). For example, when the linking group Q is —CH$_2$—, the terminal group is a biphenyl group. Alternatively, wherein the linking group is —C(CH$_3$)$_2$—, the terminal group is 4-cumyl phenyl. The monofunctional biphenyl monomer(s) also comprise a single ethylenically unsaturated group that is preferably polymerizable by exposure to (e.g. UV) radiation. The monofunctional biphenyl monomer(s) preferably comprise a single (meth)acrylate group or single thio(meth)acrylate group. Acrylate functionality is typically preferred. In some aspects, the biphenyl group is joined directly to the ethylenically unsaturated (e.g. (meth)acrylate) group. An exemplary monomer of this type is 2-phenyl-phenyl acrylate. The biphenyl mono(meth)acrylate or biphenyl thio(meth)acrylate monomer may further comprise a (e.g. 1 to 5 carbon) alkyl group optionally substituted with one or more hydroxyl groups. An exemplary species of this type is 4-biphenyl methyl acrylate.

In one embodiment, a monofunctional biphenyl (meth)acrylate monomer is employed having the general formula (III):

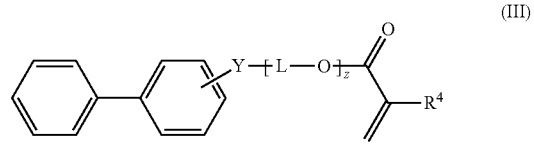

wherein R$^4$ is H or CH$_3$;

Y is O or S;

z ranges from 0 to 10 (e.g., z is 1, 2, 3, 4, 5, 6, 7, 8, 9, or 10); and

L is a divalent alkylene group having 1 to 5 carbon atoms (i.e. methylene, ethylene, propylene, butylene, or pentylene), optionally substituted with hydroxy.

One representative biphenyl (meth)acrylate monomer, 2-phenyl-phenyl acrylate, commercially available from Toagosei Co. Ltd. of Japan under the trade designation "TO-2344" is depicted as follows:

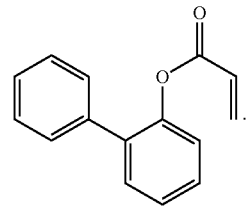 [SMILES: C=CC(=O)Oc1ccccc1-c1ccccc1]

Yet another biphenyl (meth)acrylate monomer, 2-phenyl-2-phenoxyethyl acrylate, available from Toagosei Co. Ltd. under the trade designation "TO-1463" and under the trade designation "M1142" from Miwon Specialty Chemical Co. Ltd., Korea, is depicted as follows:

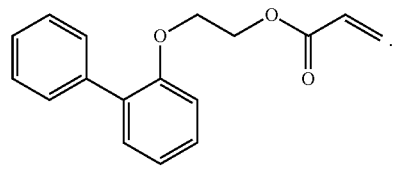 [SMILES: C=CC(=O)OCCOc1ccccc1-c1ccccc1]

In another embodiment, the monofunctional biphenyl (meth)acrylate monomer has the general formula:

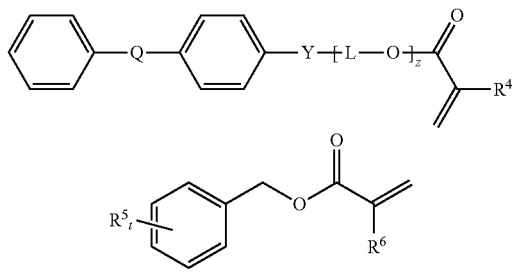

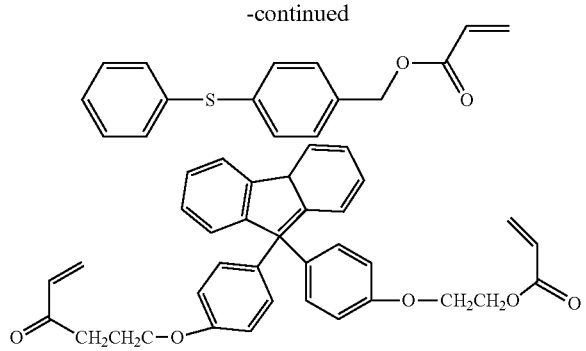

wherein $R^4$ is H or $CH_3$;
Y is O or S;
Q is selected from —$C(CH_3)_2$—, —$CH_2$—, —C(O)—, —S(O)—, and —$S(O)_2$—;
z ranges from 0 to 10 (e.g. z is 1, 2, 3, 4, 5, 6, 7, 8, 9, or 10); and
L is an alkylene group having 1 to 5 carbon atoms, optionally substituted with hydroxy.

Another biphenyl (meth)acrylate monomer is 4-(-2-phenyl-2-propyl)phenyl acrylate, available from Toagosei Co. Ltd. under the trade designation "TO-2345".

Monofunctional substituted benzyl monomers are of the general formula:

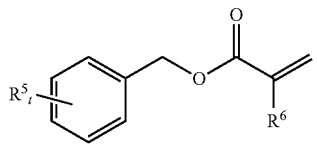

wherein at least one $R^5$ comprises an aromatic substituent, $R^6$ is hydrogen or methyl, and t is an integer from 1 to 4, meaning the ring may comprise 1, 2, 3, or 4 $R^5$ groups.

A wide variety of aromatic substituents are suitable for the $R^5$ group or groups. Typically, the at least one aromatic substituent $R^5$ comprises a substituted or unsubstituted aromatic group of the type —$CH_2$—Ar, or a heteroatom linked aromatic group of the type —X—Ar, wherein X is S or O, and each Ar is independently a substituted or unsubstituted phenyl group, a fused aromatic group, or 2 or more alkyl group-linked phenyl or substituted phenyl or substituted phenyl groups.

Thus, the $R^5$ group or groups may comprise various aromatic substituents such as:

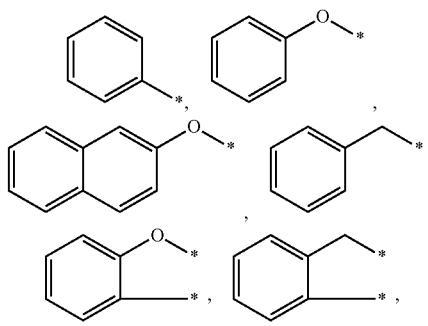

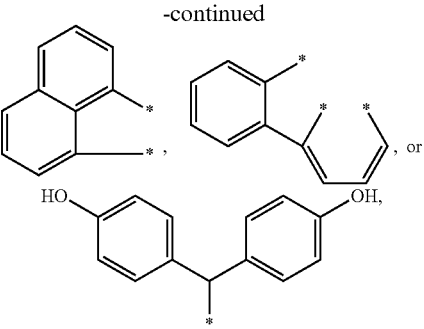

or, or *—S—Ar.

The aromatic substituent $R^5$ is generally bonded to the aromatic ring of the benzyl group by at least one divalent (e.g. alkylene or ether) linking group. In some embodiments, the aromatic substituent $R^5$ is bonded to the aromatic benzyl ring by two or more divalent (e.g. alkylene or ether) linking groups. Each * denotes the point(s) of attachment to the aromatic ring of Formula I; and Ar is a substituted or unsubstituted phenyl group, a fused aromatic group, or 2 or more alkyl group-linked phenyl or substituted phenyl groups.

In some favored embodiments, t is 1. Representative structures include:

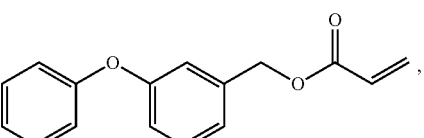

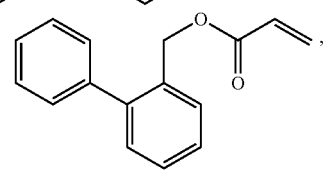

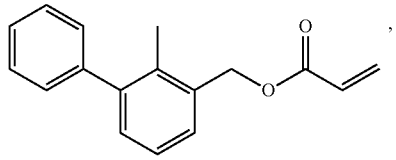

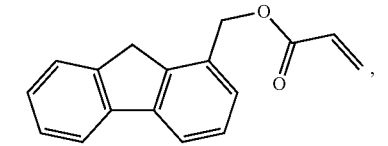

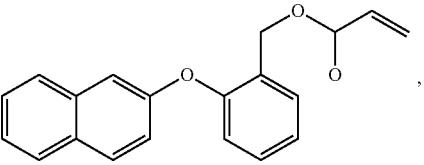

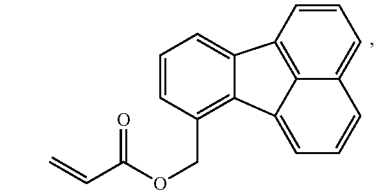

-continued

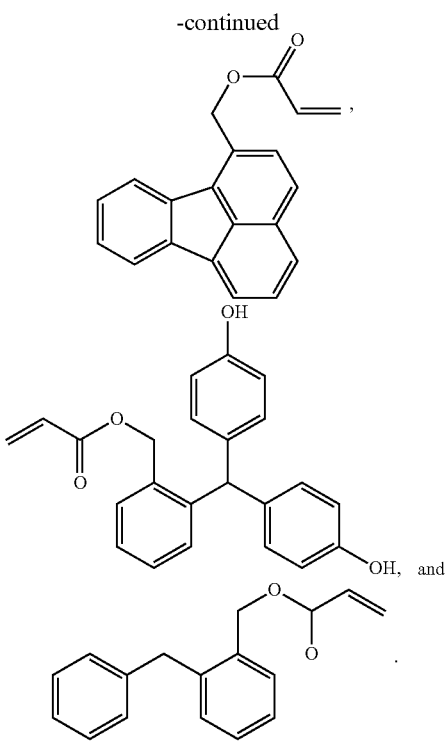

One particularly suitable monomer is one in which $R^6$ is a hydrogen, t is 1, $R^5$ is —S— phenyl. This monomer is shown below:

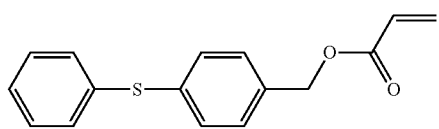

In other embodiments of the monomers, t is greater than 1. In one embodiment, t is 3.

One representative structure is:

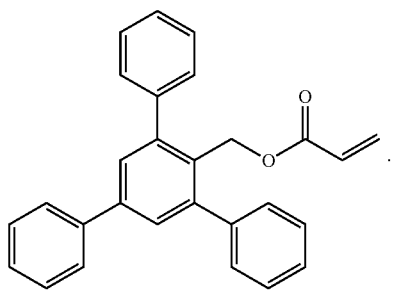 [SMILES: C=CC(=O)OCc1c(-c2ccccc2)cc(-c2ccccc2)cc1-c1ccccc1 ; "."]

Some specific monomers that are commercially available from Miwon Specialty Chemical Co. Ltd. of Korea, include 3-Phenoxy benzyl acrylate available under trade designation M1122, and 4-biphenyl methyl acrylate available from Miwon Specialty Chemicals, Exton, PA as MIRAMER M1192 or MIRAMER M1192H.

Various aromatic alcohols from Sigma-Aldrich are available as starting materials that can be converted to (meth) acrylates by reacting such materials with (meth)acrylic acid or (meth)acrylic acid derivatives.

The inclusion of monofunctional aromatic (e.g. (meth) acrylate) monomers can concurrently raise the refractive index of the organic component and improve the processability of the polymerizable composition by reducing the viscosity. These monomers are particularly advantageous when relatively high (i.e. greater than 25 wt %) concentrations of (e.g. lower refractive index) difunctional (meth) acrylate monomers or oligomers are employed.

The organic component may include a single monofunctional (meth)acrylate monomer or a combination of two or more monofunctional (meth)acrylate monomers, such as the biphenyl (meth)acrylate or substituted benzyl (meth)acrylate monomers disclosed above. The total amount of such monofunctional monomers is generally at least 10 wt %, 15 wt %, 20 wt % or 25 wt % of the organic component. The total amount of monofunctional monomers is no greater than 90 wt %, and more typically no greater than about 75 wt % (e.g. less than 70 wt %, 65 wt %, 60 wt %). In some embodiments, the total amount of monofunctional monomer(s) ranges from 30 wt % to 50 wt % of the organic component.

The polymerizable resin composition may comprise at least 1% or 5% and up to 10, 15, 20%, or even 30 wt % of one or more monomers or oligomers having at least two polymerizable (meth)acrylate groups. A variety of monomers and/or oligomers having at least two polymerizable (meth)acrylate groups may be employed. Various difunctional (meth)acrylate monomers are known in the art, including for example 1,3-butylene glycol diacrylate, 1,4-butanediol diacrylate, 1,6-hexanediol diacrylate, 1,6-hexanediol monoacrylate monomethacrylate, ethylene glycol diacrylate, alkoxylated aliphatic diacrylate, alkoxylated cyclohexane dimethanol diacrylate, alkoxylated hexanediol diacrylate, alkoxylated neopentyl glycol diacrylate, neopentylglycol hydroxypivalate diacrylate, cyclohexanedimethanol diacrylate, diethylene glycol diacrylate, dipropylene glycol diacrylate, ethoxylated bisphenol A diacrylate, neopentyl glycol diacrylate, polyethylene glycol diacrylate, (Mn=200 g/mole, 400 g/mole, 600 g/mole), propoxylated neopentyl glycol diacrylate, tetraethylene glycol diacrylate, tricyclodecanedimethanol diacrylate, triethylene glycol diacrylate, and tripropylene glycol diacrylate.

Suitable difunctional urethane (meth)acrylates are commercially available from Sartomer under the trade designations "CN965", "CN968", "CN981", "CN 983", "CN 984", "CN972", and "CN978"; from Cognis under the trade designation "PHOTOMER 6210", "PHOTOMER 6217", "PHOTOMER 6230", "PHOTOMER 6623", "PHOTOMER 6891", and "PHOTOMER 6892"; and from UCB under the trade designations "EBECRYL 1290", "EBECRYL 2001", and "EBECRYL 4842".

Suitable difunctional polyester (meth)acrylates are commercially available from Sartomer under the trade designation "CN292"; from Cognis under the trade designation "PHOTOMER 5010", "PHOTOMER 5429", "PHOTOMER 5430", "PHOTOMER 5432", "PHOTOMER 5662", "PHOTOMER 5806", and "PHOTOMER 5920"; and from UCB under the trade designations "EBECRYL 80", "EBECRYL 81", "EBECRYL 83", "EBECRYL 450", "EBECRYL 524", "EBECRYL 525", "EBECRYL 585", "EBECRYL 588", "EBECRYL 810", and "EBECRYL 2047".

Suitable (meth)acrylated acrylic oligomers are also commercially available or can be prepared by methods know in the art.

The polymerizable composition may comprise an aromatic difunctional (meth)acrylate monomer that comprises a major portion having the following general structure:

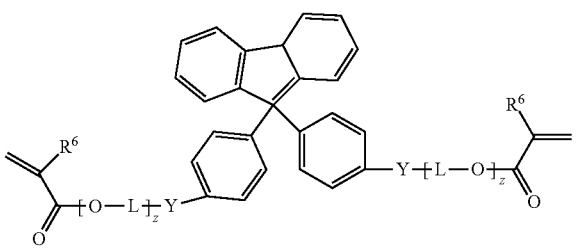

wherein each $R^4$ is independently hydrogen or methyl. Each $R^5$ is independently hydrogen or bromine. Each Q is independently —C(CH$_3$)$_2$—, —CH$_2$—, —C(O)—, fluorene, —S—, —S(O)—, or —S(O)$_2$—, and each Y is independently O or S. In some embodiments Q is preferably —C(CH$_3$)$_2$— and Y is preferably O. Typically, the $R^4$ groups are the same. Typically, the $R^5$ groups are the same as each other as well. Z independently ranges from 0 to 10 (e.g. z is 1, 2, 3, 4, 5, 6, 7, 8, 9, or 10); and L is an alkylene group having 1 to 5 carbon atoms, optionally substituted with hydroxy. Typically, z is the same. An exemplary difunctional (meth)acrylate monomer is the fused aromatic compound bisphenol fluorene diacrylate such as in the following formula:

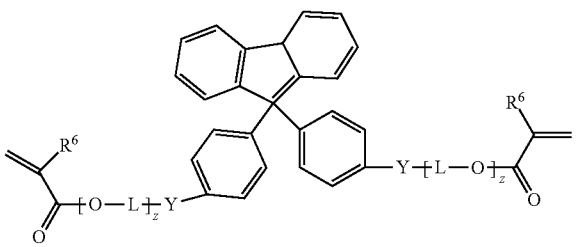

Where $R^6$ is H or —CH$_3$

Z independently ranges from 0 to 10 (e.g. z is 1, 2, 3, 4, 5, 6, 7, 8, 9, or 10); and L is an alkylene group having 1 to 5 carbon atoms, optionally substituted with hydroxy. Such a compound is commercially available as part of a curable mixture from Miwon Specialty Chemicals, Exton, PA as "HR 6042" and which has the structure:

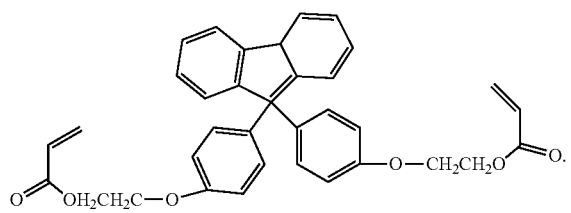

The di(meth)acrylate monomer may be synthesized or purchased. As used herein, major portion refers to at least 60-70 wt % of the monomer containing the specific structure(s) just described. It is commonly appreciated that other reaction products are also typically present as a byproduct of the synthesis of such monomers.

Various (meth)acrylated aromatic epoxy oligomers are commercially available. For example, (meth)acrylated aromatic epoxy, (described as a modified epoxy acrylates), are available from Sartomer, Exton, PA under the trade designation "CN118", and "CN115". (Meth)acrylated aromatic epoxy oligomer, (described as an epoxy acrylate oligomer), is available from Sartomer under the trade designation "CN2204". Further, an (meth)acrylated aromatic epoxy oligomer, (described as an epoxy novolak acrylate blended with 40% trimethylolpropane triacrylate), is available from Sartomer under the trade designation "CN112C60".

In some embodiments, the aromatic epoxy acrylate is derived from bisphenol A, such as those of the structure previously described. In other embodiments, the aromatic epoxy acrylates are derived from a different monomer than bisphenol A.

One exemplary bisphenol-A ethoxylated diacrylate monomer is commercially available from Sartomer under the trade designations "SR602" (reported to have a viscosity of 610 cps at 20° C. and a Tg of 2° C.). Another exemplary bisphenol-A ethoxylated diacrylate monomer is as commercially available from Sartomer under the trade designation "SR601" (reported to have a viscosity of 1080 cps at 20° C. and a Tg of 60° C.).

In one embodiment, the monomer in the organic component comprises an aryl group which is the same aryl group as in $R^3$ in Formula II above. In one embodiment, the monofunctional aromatic monomer in the organic component comprises at least one of a phenyl, phenoxy, biphenyl, naphthyl, thiophenyl, carbazole, cumyl phenoxyl (bisphenol A), benzylphenyl, phenoxy phenyl, fluorenyl, thiophenyl benzyl, and dibenzofuran. It has been discovered that by matching the aryl end groups of the monomers in the organic component and the $R^3$ groups of Formula II, surface modified inorganic particles what are stable and/or enable higher particle loadings can be achieved.

In one embodiment, the polymerizable composition comprises at least 10, 20, or even 30% by weight and at most 40, 50, 60, 70, 80, 90, or even 100% by weight of the surface modified inorganic particles.

The organic component optionally comprises up to about 50 wt % (e.g. any amount ranging from 0 to 50) reactive diluents. Reactive diluents are mono-ethylenically unsaturated monomers such as (meth)acrylates or monomeric N-substituted or N,N-disubstituted (meth)acrylamides, especially an acrylamide. These include N-alkylacrylamides and N,N-dialkylacrylamides, especially those containing $C_{1-4}$ alkyl groups. Examples are N-isopropylacrylamide, N-t-butylacrylamide, N,N-dimethylacrylamide, N,N-diethylacrylamide, N-vinyl pyrrolidone and N-vinyl caprolactam.

Suitable reactive diluents include for example phenoxy ethyl (meth)acrylate; phenoxy-2-methylethyl (meth)acrylate; phenoxyethoxyethyl (meth)acrylate, 3-hydroxy-2-hydroxypropyl (meth)acrylate; benzyl (meth)acrylate; phenylthio ethyl acrylate; 2-naphthylthio ethyl acrylate; 1-naphthylthio ethyl acrylate; 2,4,6-tribromophenoxy ethyl acrylate; 2,4-dibromophenoxy ethyl acrylate; 2-bromophenoxy ethyl acrylate; 1-naphthyloxy ethyl acrylate; 2-naphthyloxy ethyl acrylate; phenoxy 2-methylethyl acrylate; phenoxyethoxyethyl acrylate; 3-phenoxy-2-hydroxy propyl acrylate; 2,4-dibromo-6-sec-butylphenyl acrylate; 2,4-dibromo-6-isopropylphenyl acrylate; benzyl acrylate; phenyl acrylate; 2,4,6-tribromophenyl acrylate. Other high refractive index monomers such as pentabromobenzyl acrylate and pentabromophenyl acrylate can also be employed.

The aromatic (meth)acrylate monomer(s) are typically employed in combination with (e.g. up to 25 wt % of) a monofunctional reactive diluent(s) having a lower refractive index than the biphenyl monomer(s).

A preferred diluent is phenoxyethyl (meth)acrylate, and in particular phenoxyethyl acrylate (PEA). Phenoxyethyl acrylate is commercially available from more than one source including from Sartomer under the trade designation "SR339"; from Eternal Chemical Co. Ltd. under the trade designation "ETERMER 210"; and from Toagosei Co. Ltd under the trade designation "TO-1166". Benzyl acrylate is commercially available from AlfaAeser Corp, Ward Hill, MA.

The organic component may optionally comprise a crosslinker that comprises at least three (meth)acrylate groups. In some embodiments, the crosslinker may be present in the polymerizable composition in an amount of at least about 5, 6, 7, or even 10 wt %; and at most 10, 15, 20, or even 25 wt %.

Suitable crosslinking agents include for example pentaerythritol tri(meth)acrylate, pentaerythritol tetra(meth)acrylate, trimethylolpropane tri(methacrylate), dipentaerythritol penta(meth)acrylate, dipentaerythritol hexa(meth)acrylate, trimethylolpropane ethoxylate tri(meth)acrylate, glyceryl tri(meth)acrylate, pentaerythritol propoxylate tri(meth)acrylate, and ditrimethylolpropane tetra(meth)acrylate. Any one or combination of crosslinking agents may be employed. Since methacrylate groups tend to be less reactive than acrylate groups, the crosslinker(s) are preferably free of methacrylate functionality.

In one embodiment, the crosslinker comprises an alkylene oxide repeat, such as ethylene oxide repeat units.

Various crosslinkers are commercially available. For example, pentaerythritol triacrylate (PETA) is commercially available from Sartomer Company, under the trade designation "SR444", from Osaka Organic Chemical Industry, Ltd. Osaka, Japan under the trade designation "VISCOAT #300", from Toagosei Co. Ltd., Tokyo, Japan under the trade designation "ARONIX M-305", and from Eternal Chemical Co., Ltd., Kaohsiung, Taiwan under the trade designation "ETERMER 235". Trimethylol propane triacrylate (TMPTA), depicted as follows, is commercially available from Sartomer Company under the trade designations "SR351" and from Toagosei Co. Ltd. under the trade designation "ARONIX M-309".

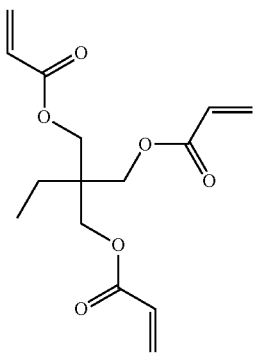 [SMILES: C=CC(=O)OCC(CC)(COC(=O)C=C)COC(=O)C=C]

Ethoxylated trimethylolpropane triacrylate and ethoxylated pentaerythritol tetraacrylate crosslinkers are commercially available from Sartomer under the trade designations "SR454" and "SR494" respectively. SR454 is depicted as follows:

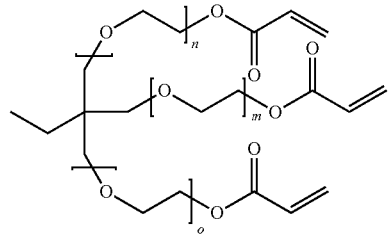

wherein n+m+o is about 3.

In some embodiments, the organic component comprises less than 5, 2, 1, or even 0.5 wt % crosslinker or is free of crosslinker.

In some embodiments, it is preferred that the polymerizable resin composition is substantially free (i.e. contain less than 1, 0.5, or even 0.1 wt %) or is free of bromine. In other embodiments, the total amount of bromine in combination with chlorine is less than 1, 0.5, or even 0.1 wt %. In some aspects, the polymerizable resin composition is substantially non-halogenated (i.e. contains less than 1, 0.5, or even 0.1 wt % total of bromine, chlorine, fluorine and iodine).

The polymerizable composition may be cured via thermal or ultraviolet (UV) radiation. In the case of UV radiation, the polymerizable compositions comprise at least one photoinitiator. A single photoinitiator or blends thereof may be employed. In general, the photoinitiator(s) are at least partially soluble (e.g. at the processing temperature of the resin) and substantially colorless after being polymerized. The photoinitiator may be (e.g. yellow) colored, provided that the photoinitiator is rendered substantially colorless after exposure to the UV light source.

Suitable photoinitiators include monoacylphosphine oxide and bisacylphosphine oxide. Commercially available mono or bisacylphosphine oxide photoinitiators include 2,4,6-trimethylbenzoybiphenylphosphine oxide, commercially available from BASF (Charlotte, NC) under the trade designation "LUCIRIN TPO"; ethyl-2,4,6-trimethylbenzoylphenyl phosphinate, also commercially available from BASF under the trade designation "LUCIRIN TPO-L"; and bis(2,4,6-trimethylbenzoyl)-phenylphosphine oxide commercially available from Ciba Specialty Chemicals under the trade designation "IRGACURE 819". Other suitable photoinitiators include 2-hydroxy-2-methyl-1-phenyl-propan-1-one, commercially available from Ciba Specialty Chemicals under the trade designation "DAROCUR 1173" as well as other photoinitiators commercially available from Ciba Specialty Chemicals under the trade designations "DAROCUR 4265", "IRGACURE 651", "IRGACURE 1800", "IRGACURE 369", "IRGACURE 1700", and "IRGACURE 907".

The photoinitiator can be used at a concentration of at least 0.1, 0.5, or even 1 wt % and at most 2, 3, 5 or even 10 wt % versus the polymerizable composition. Greater than 5 wt % of the photoinitiator is generally disadvantageous in view of the tendency to cause yellow discoloration of the resulting polymerized article. Other photoinitiators may also suitably be employed as may be determined by one of ordinary skill in the art.

Surfactants such as fluorosurfactants and silicone based surfactants can optionally be included in the polymerizable composition to reduce surface tension, improve wetting, allow smoother coating and fewer defects of the coating, etc.

The surface modified particles can be incorporated into the polymerizable (or curable) compositions in various methods. In a preferred aspect, a solvent exchange procedure is utilized whereby the organic component is added to the surface modified sol, followed by removal of the water and co-solvent (if used) via evaporation, thus leaving the particles dispersed in the polymerizable resin. The evaporation step can be accomplished for example, via distillation, rotary evaporation or oven drying. In another aspect, the surface modified particles can be extracted into a water immiscible solvent followed by solvent exchange, if so desired. Alternatively, another method for incorporating the surface modified particles in the organic component involves the drying of the modified particles into a powder, followed by the addition of the organic component into which the particles are dispersed. The drying step in this method can be accomplished by conventional means suitable for the system, such as, for example, oven drying or spray drying.

In one embodiment, the polymerizable composition is substantially solvent free meaning having less than 5, 3, 2, 1, 0.5, 0.1, or even 0.01 wt % of solvent, wherein a solvent is defined as a volatile, non-reactive (e.g., non-polymerizable) organic compound, such as acetonitrile, triethylamine, alcohol, etc. The concentration of solvent can be determined by known methods, such as gas chromatography.

In one embodiment, the polymerizable composition is stable, meaning that when left to sit at ambient conditions for at least 24 hours, there is no visible separation between the surface modified inorganic particles and the organic component.

Applications

Because the polymerizable compositions disclosed herein have high refractive indices while also having decreased viscosities, these polymerizable compositions may be used in optical applications such as in coating or casting films or in printing applications, where layers of the resulting composite material are adjacent to inorganic layers.

The polymerizable compositions disclosed herein may be used in making a microstructured film (as described in U.S. Pat. No. 8,821,770 Jones et al. and U.S. Pat. No. 4,576,850 both herein incorporated by reference) or used to make a planar coating (as described in U.S. patent application Ser. No. 16/473,841, Swartz et al. herein incorporated by reference).

In one embodiment, the resulting polymerized (or cured) compositions of the present disclosure are translucent or transparent. The composition may be substantially transparent (e.g., a layer of the polymerized composition may transmit at least 80 percent, or at least 90 percent of light in the wavelength range of 400 to 700 nm).

In one embodiment, the resulting polymerized (or cured) compositions of the present disclosure are stable, meaning that if left to sit at ambient conditions, where is no visible separation between the organic component and the inorganic particles for at least 24, 28, 36, 72, or even 150 hours.

In one embodiment, the polymerizable composition is used to as a curable ink, which allows for precise printing of the polymerizable composition onto a substrate, followed by polymerization of the composition to form a composite layer (continuous or discontinuous) along the surface of the substrate, for example an inorganic substrate or a polymeric substrate.

EXAMPLES

Unless otherwise noted or readily apparent from the context, all parts, percentages, ratios, etc. in the Examples and the rest of the specification are by weight. Chemicals not listed in the materials table were obtained from VWR International (Radnor, PA).

TABLE 1

Materials List

| Abbreviation | Description and Source |
| --- | --- |
| Benzyl Acrylate | Benzyl acrylate, available under trade designation "MIRAMER M1182", was obtained from Miwon Specialty Chemical Company, Ltd. (Korea). |
| Mercaptosuccinic acid | (±)-Mercaptosuccinic acid, 98%, was obtained from Alfa Aesar (Tewksbury, MA). |
| M1192 | 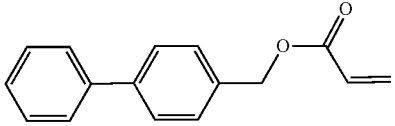 [SMILES: C=CC(=O)OCc1ccc(-c2ccccc2)cc1] Refers to biphenylmethyl acrylate available under trade designation "MIRAMER M1192", obtained from Miwon Specialty Chemical Company, Ltd. (Korea). |
| PTPBA | para-Thiophenyl benzyl acrylate, prepared according to the Synthesis 1 disclosed in WO2018122748 (Schwartz, et al.). |
| 2-phenoxyethyl acrylate | 2-phenoxyethyl acrylate available under trade designation "SR 339" was obtained from Arkema, Inc. (France). |
| SR 454 | Ethoxylated trimethylolpropane triacrylate available under trade designation "SR 454", obtained from Arkema, Inc. (France). |
| Zirconia sol | Dispersion of zirconia nanoparticles in water, prepared according to the procedure disclosed in Example 1 of U.S. Pat. No. 8,821,770 (Jones, et al.) |
| Surface Treatment 1 | Refers to Example 1 in patent U.S. Pat. No. 8,821,770 (Jones, et al.) |

Test Method 1: Refractive Index

The refractive index of the polymerizable compositions was measured using a refractometer (Model 33-46-10, Bausch and Lomb, having a broad spectrum white light source) calibrated with a certified refractive index liquid available from Cargille Labs, Cedar Grove, NJ.

Test Method 2: Viscosity

The viscosity was measured at 55° C. and a shear rate of 1000/s using a Discovery HR-2 Rheometer from TA Instruments (New Castle, DE).

Example 1: Synthesis of a Benzyl Acrylate-Derived Dicarboxylic Acid

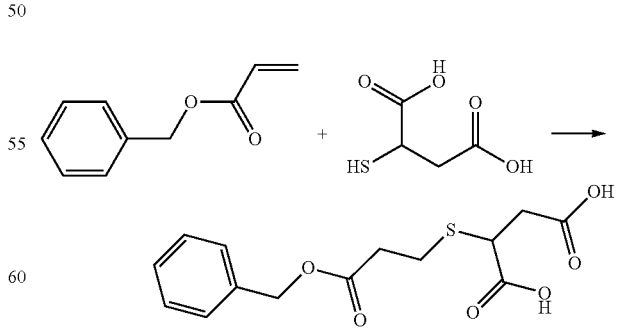

A 2 L roundbottom flask was charged with mercaptosuccinic acid (101 g, 673 mmol), benzyl acrylate (105 g, 647 mmol), and acetonitrile (400 g). The mixture with stirred with a magnetic stir bar until the solids dissolved completely. Triethylamine (144 g, 1.42 mol) was added slowly with stirring. The solution was allowed to stir for 2 days at room temperature. The acetonitrile and excess triethylamine were removed by distillation at reduced pressure using a rotary evaporator. The remaining viscous oil was treated with aqueous HCl (3.0 M, 600 mL) and diethyl ether (800 mL). The mixture was transferred to a separatory funnel and the layers were separated. The organic layer was washed with dilute aqueous HCl (0.2 M, 600 mL), dried over anhydrous sodium sulfate, and filtered. Concentration at reduced pressure using a rotary evaporator yielded 200.0 g (99% yield) of clear oil that crystallized over days into a white solid.

Example 2: Synthesis of a Dicarboxylic Acid Derived from M1192

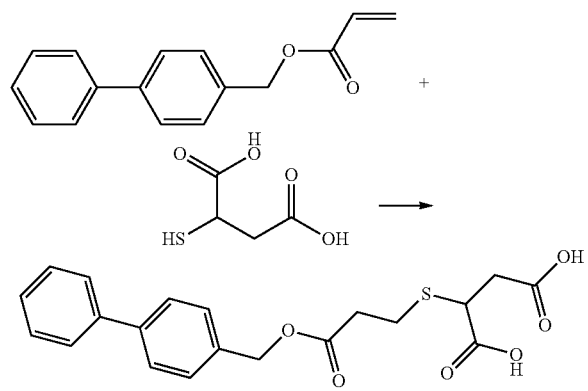

A 1 L roundbottom flask was charged with mercaptosuccinic acid (33.4 g, 222 mmol), M1192 (48.2 g, 202 mmol), acetonitrile (250 g), and triethylamine (81.9 g, 809 mmol). The resulting solution was immersed in an oil bath held at 50° C. for 120 minutes, then allowed to cool. The acetonitrile and excess triethylamine were removed by distillation at reduced pressure using a rotary evaporator. The remaining viscous oil was treated with aqueous HCl (2.3 M, 400 mL) and methyl tert-butyl ether (400 mL). The mixture was transferred to a separatory funnel and the layers were separated. The organic layer was washed with dilute aqueous HCl (0.2 M, 200 mL), dried over anhydrous sodium sulfate, and filtered. Concentration at reduced pressure using a rotary evaporator yielded 88.9 g of clear oil that crystallized slowly into a white solid.

Example 3: Synthesis of a Dicarboxylic Acid Derived from PTPBA

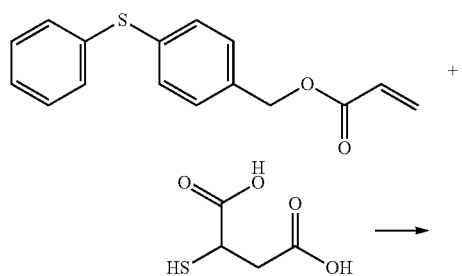

-continued

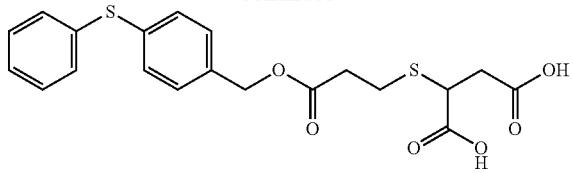

A 250 mL roundbottom flask was charged with mercaptosuccinic acid (9.16 g, 61.0 mmol), PTPBA (15.0 g, 55.5 mmol), acetonitrile (50 g), and triethylamine (22.5 g, 222 mmol). The solution was immersed in an oil bath held at 50° C. for 45 minutes, then allowed to cool overnight. The acetonitrile and excess triethylamine were removed by distillation at reduced pressure using a rotary evaporator. The remaining viscous oil was treated with aqueous HCl (1.0 M, 250 mL) and diethyl ether (150 mL). The mixture was transferred to a separatory funnel and the layers were separated. The organic layer was washed with dilute aqueous HCl (0.2 M, 150 mL), dried over anhydrous sodium sulfate, and filtered. Concentration at reduced pressure using a rotary evaporator yielded 22.7 g (97% yield) of light brown oil that crystallized slowly into a white solid.

Example 4: Synthesis of a Dicarboxylic Acid Derived from 2-Phenoxyethyl Acrylate

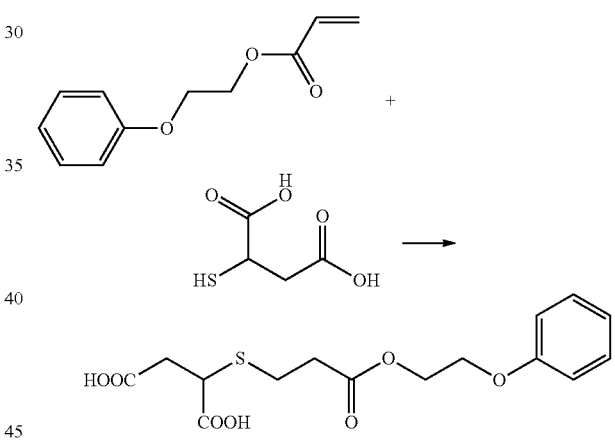

A 250 mL roundbottom flask was charged with mercaptosuccinic acid (12.3 g, 82.0 mmol), 2-phenoxyethyl acrylate (15.0 g, 78.1 mmol), acetonitrile (40 g), and triethylamine (23.7 g, 234 mmol). The solution was stirred at room temperature for 1 hour. The acetonitrile and excess triethylamine were removed by distillation at reduced pressure using a rotary evaporator. The remaining viscous oil was treated with aqueous HCl (1.0 M, 250 mL) and diethyl ether (200 mL). The mixture was transferred to a separatory funnel and the layers were separated. The organic layer was washed with dilute aqueous HCl (0.2 M, 200 mL), dried over anhydrous sodium sulfate, and filtered. Concentration at reduced pressure using a rotary evaporator yielded 21.5 g (81% yield) of clear oil that crystallized slowly into a white solid.

Examples 5-10: Surface Modification of Zirconia Nanoparticles and Dispersion in Acrylate Resin Polymerizable Resin Compositions were made as described below. The following materials were added to a vessel, in the amounts required to achieve the resin compositions described in Table 2: zirconia sol and an approximately equal weight of 1-methoxy-2-propanol, the surface modifier specified in Table 2 and diluted to 25 wt % in 1-methoxy-2-propanol, and the acrylates specified in Table 3. Water and alcohol were removed via vacuum distillation.

TABLE 2

Zirconia Dispersion Formulations

| Example | Zirconia Surface Modifier | Mass % Zirconia | Mass % Surface Modifier | Mass % M1192 | Mass % SR454 |
|---|---|---|---|---|---|
| Comparative Example 1 | Surface Treatment 1 | 60.0% | 14.3% | 24.9% | 0.8% |
| Example 5 | Example 1 | 55.0% | 12.0% | 32.0% | 0.7% |
| Example 6 | Example 1 | 52.0% | 11.4% | 35.5% | 0.8% |
| Example 7 | Example 2 | 55.0% | 12.8% | 31.2% | 0.7% |
| Example 8 | Example 2 | 52.0% | 14.1% | 32.9% | 0.7% |
| Example 9 | Example 3 | 55.0% | 13.9% | 30.2% | 0.7% |
| Example 10 | Example 3 | 52.0% | 13.1% | 33.8% | 0.8% |

The refractive index and viscosity of each comparative and inventive example resin blend was measured. The results are shown in Table 3. All samples, when left to sit for at least 24 hours at ambient conditions, showed no visible separation between the organic components and the surface modified zirconia.

TABLE 3

Refractive Index and Viscosity of Zirconia Dispersions

| Sample | Zirconia Surface Modifier | Refractive Index | Viscosity at 55° C. |
|---|---|---|---|
| Comparative Example 1 | Surface Treatment 1 | 1.671 | 455 cP |
| Example 5 | Example 1 | 1.681 | 899 cP |
| Example 6 | Example 1 | 1.690 | 2224 cP |
| Example 7 | Example 2 | 1.673 | 220 cP |
| Example 8 | Example 2 | 1.691 | 1397 cP |
| Example 9 | Example 3 | 1.673 | 204 cP |
| Example 10 | Example 3 | 1.691 | 922 cP |

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:
1. A dicarboxylic acid compound of formula (I)

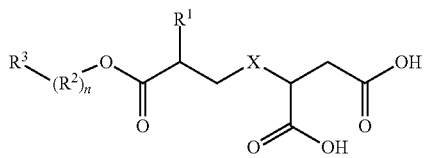

wherein:
$R^3$ comprises a monovalent aromatic group,
$R^2$ is an alkylene group comprising 1 to 6 carbon atoms,
n is 0 or 1,
$R^1$ is H or $CH_3$, and
X is S or NZ, wherein Z is H, an alkyl group comprising 1 to 4 carbon atoms, or a phenyl group.

2. The compound of claim 1, wherein the aryl group comprises at least one of a phenyl, phenoxy, biphenyl, naphthyl, thiophenyl, carbazole, cumyl phenoxyl (bisphenol A), benzyl phenyl, phenoxy phenyl, fluorenyl, thiophenyl benzyl, and dibenzofuran.

3. The compound according to claim 1, wherein $R^3$ is a phenyl, phenoxy phenyl, cumyl phenoxy, benzyl phenyl, naphthyloxy, benzophenone oxy, fluorenyl, thiophenyl phenyl, diphenyl phenoxy, carbazole, or thionaphthyl group.

4. The compound according to claim 1, wherein n is 0 and $R^3$ is a phenyl, benzyl phenyl, biphenyl, fluorenyl, or naphthyl group.

5. The compound of claim 1, wherein the dicarboxylic acid compound is selected from:

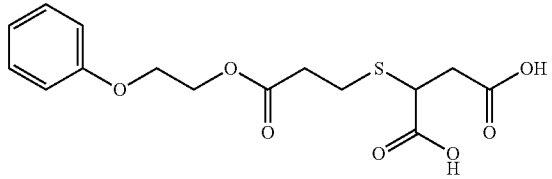

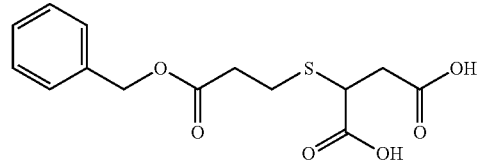

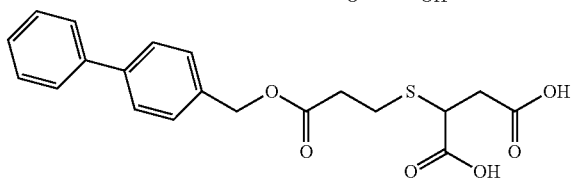

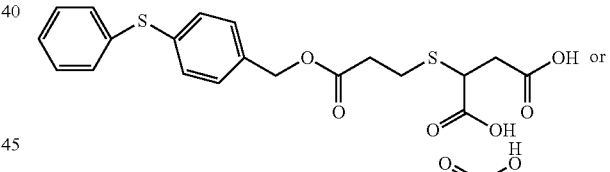 or

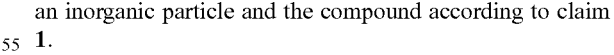

6. A particle composition comprising a reaction product of an inorganic particle and the compound according to claim 1.

7. The particle composition of claim 6, wherein the inorganic particle comprises at least one of a metal oxide, and a chalcogenide.

8. The particle composition of claim 7, wherein the metal oxide is titanium oxide, zirconium oxide, aluminum oxide, hafnium oxide, cerium oxide, niobium oxide, and combinations thereof.

9. The particle composition of claim 7, wherein the chalcogenide is zinc sulfide.

10. The particle composition of claim 6, wherein the inorganic particle has an average diameter of at least 2 nm and at most 1 micron.

11. The particle composition of claim 6, wherein at least 10% by weight of the compound according to Formula I is used versus the weight of the inorganic particle.

12. A particle composition comprising a surface modified inorganic particle, wherein the surface of an inorganic particle is modified with a plurality of the following groups of Formula II:

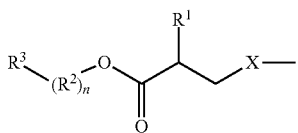

wherein
R³ comprises an aryl group,
R² is an alkylene group comprising 1 to 6 carbon atoms,
n is 0 or 1,
R¹ is H or CH₃, and
X is S or NZ, wherein Z is H or alkyl group comprising 1 to 4 carbon atoms or a phenyl group.

13. The particle composition of claim 12, wherein the groups of Formula II are selected from:

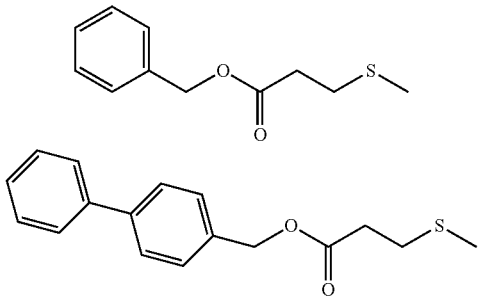

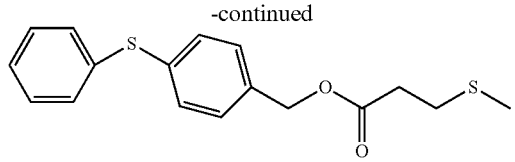

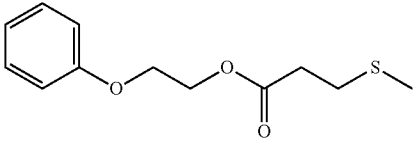

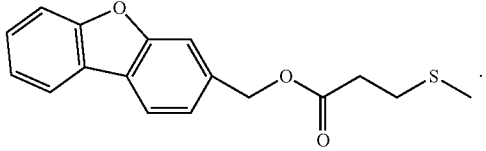

14. The particle composition of claim 12, wherein the inorganic particle has an average diameter of at least 5 nm and at most 50 nm.

15. A polymerizable composition comprising: the particle composition of claim 12; and a monofunctional aromatic monomer.

16. The polymerizable composition of claim 15, wherein the monofunctional aromatic monomer comprises at least one of a phenyl, phenoxy, biphenyl, naphthyl, thiophenyl, carbazole, cumyl phenoxyl (bisphenol A), benzylphenyl, phenoxy phenyl, fluorenyl, thiophenylphenyl, and dibenzofuran.

17. The polymerizable composition of claim 16, wherein the aromatic group of the monofunctional aromatic monomer is the same as the aryl group of R³.

18. The polymerizable composition of claim 15, wherein the polymerizable composition has a viscosity of less than 30 cP at 60° C.

19. An optical article comprising the reaction product of the polymerizable composition according to claim 15.

* * * * *